United States Patent [19]

Sakakibara et al.

[11] 4,268,665
[45] May 19, 1981

[54] DERIVATIVES OF ANTIBIOTIC TYLOSIN

[75] Inventors: Hideo Sakakibara, Mishima; Tatsuro Fujiwara, Shizuoka; Osamu Okegawa, Shizuoka; Toshiyuki Watanabe, Shizuoka; Susumu Watanabe, Shizuoka; Tetsuo Matsuda, Shizuoka, all of Japan

[73] Assignee: Toyo Jozo Kabushiki Kaisha, Shizuoka, Japan

[21] Appl. No.: 75,661

[22] Filed: Sep. 14, 1979

[30] Foreign Application Priority Data

Sep. 14, 1978 [JP] Japan .................................. 53-113023
Feb. 27, 1979 [JP] Japan .................................. 54-22340

[51] Int. Cl.³ ........................ A61K 31/71; C07H 17/08
[52] U.S. Cl. .................................. 536/17 R; 424/180; 536/4
[58] Field of Search ...................... 536/9, 17 R, 17 AB

[56] References Cited

U.S. PATENT DOCUMENTS 4,017,607  4/1977  Inouye et al. ........................ 536/17
4,092,473  5/1978  Okamoto et al. ..................... 536/17

Primary Examiner—Johnnie R. Brown
Attorney, Agent, or Firm—Young & Thompson

[57] ABSTRACT

Derivatives of antibiotic tylosin of the formula

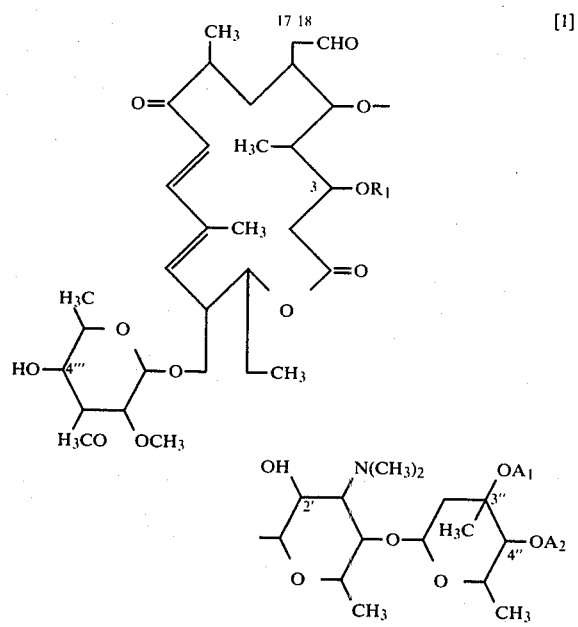

wherein $R_1$ is hydrogen or lower alkanoyl, $A_1$ and $A_2$ are groups of which one is $R_2$ and the other is $R_3$, and $R_2$ and $R_3$ are $C_{2-6}$ alkanoyl, or a physiologically acceptable salt thereof, have enhanced antibacterial activity against macrolide antibiotic-resistant strains.

8 Claims, No Drawings

DERIVATIVES OF ANTIBIOTIC TYLOSIN

This invention relates to novel derivatives of antibiotic tylosin. More particularly this invention relates to compounds of the formula

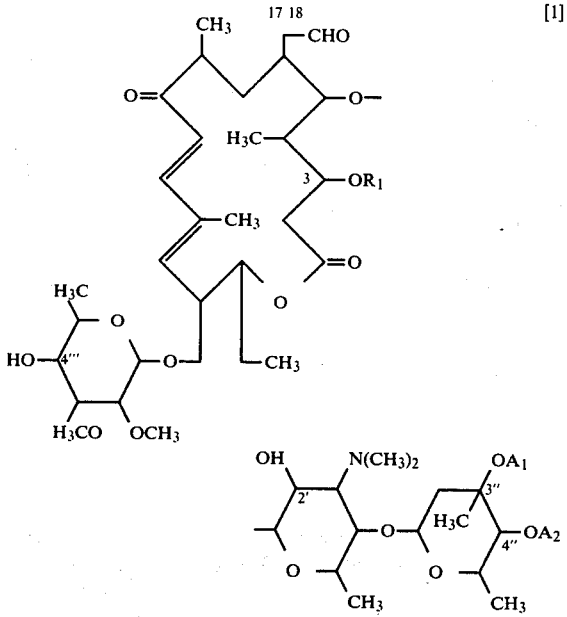

wherein $R_1$ is hydrogen or lower alkanoyl, $A_1$ and $A_2$ are groups of which one is $R_2$ and the other is $R_3$, and $R_2$ and $R_3$ are $C_{2-6}$ alkanoyl, or a physiologically acceptable salt thereof.

Preferred examples of the salt are inorganic salts such as hydrochloride, sulfate or phosphate, or organic salts such as acetate, propionate, tartrate, citrate, succinate, malate, aspartate or glutamate. Other non-toxic salts are also included.

The novel compounds [1] have the equivalent levels of antibacterial activities of prior known antibiotic tylosin, and also have enhanced antibacterial activities against all macrolide antibiotic-resistant strains such as macrolide-resistant A group strains (clinical isolates of etythromycin, oleandomycin and 16-membered macrolide antibiotic resistant strains), B group strains and C group strains. Especially the said novel compounds have superior antibacterial activities against resistant strains as compared with known 4''-acyltylosin or 3-acetyl or propionyl-4''-acyltylosins effective against strains resistant to the macrolide antibiotics. Moreover, the strong continuous bitter taste that generally characterizes macrolide antibiotics is decreased, and hence syrups for infants, who cannot be administered tablets or capsules, can be advantageously prepared. The antibiotics [1] of the present invention will be expected to show an excellent clinical infectious therapeutic effect. Furthermore, the present antiobiotics are useful for veterinary use or feed additives.

Tylosin has five hydroxyl groups at positions 3, 2', 3'', 4'' and 4'''. Among these, hydroxyl groups at positions 3, 2', 4'' and 4''' are easily acylated, and the hydroxyl group at postion 3'' is inactive. Even if the hydroxyl group at position 3' is acylated, the other positions of highly active hydroxyl groups are also acylated, and therefore acylation at both of positions 3'' and 4'' has been impossible by the prior known acylation process.

In the course of acylation of the hydroxyl group at position 3'', other hydroxyl groups, especially at positions 3, 2' and 4''' are acylated with protective groups which are selectively removed after acylation of the hydroxyl group at position 3''. Preferably protective groups are lower alkanoyl groups for the hydroxyl group at position 2', and lower alkanoyl, halogenated acetyl or trimethylsilyl groups for the hydroxyl group at position 4''. The hydroxyl group at position 3 can be protected by reacting with an aliphatic carboxylic acid anhydride in the presence of an inorganic base to form a ring

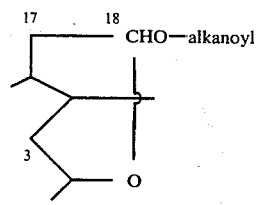

thereby to complete the present invention.

The compound [1] of the present invention can be produced by the following processes:

Process A: A compound wherein $R_1$ is hydrogen, i.e. a compound of the formula

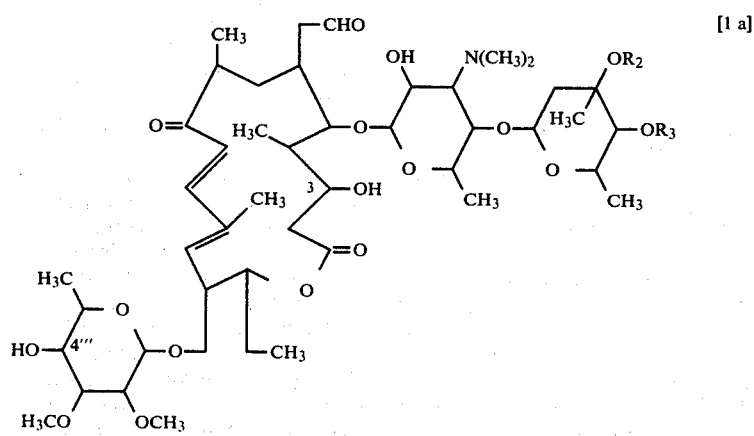

wherein $R_2$ and $R_3$ have the same meanings hereinbefore, is produced by the following method:

Tylosin, or tylosin with the 4'''-hydroxyl group protected, is reacted with an aliphatic carboxylic acid anhydride in the presence of an inorganic base to obtain a compound of the formula

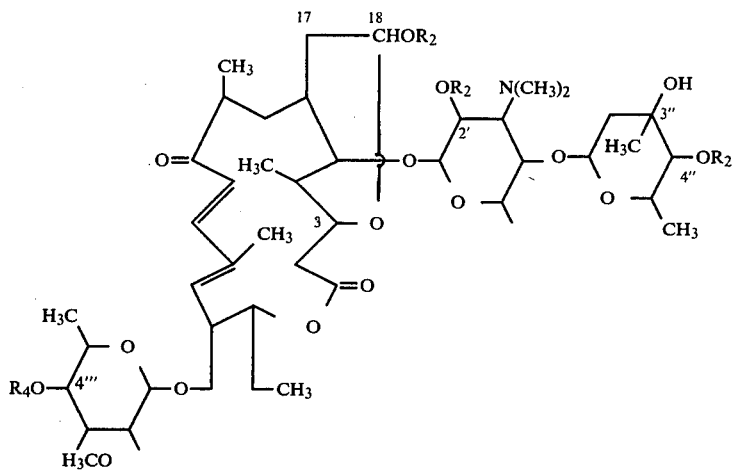

[2]

wherein $R_4$ is lower alkanoyl or halo lower alkanoyl and $R_2$ has the same meaning hereinbefore, and the said compound [2] is reacted with an aliphatic carboxylic acid anhydride under heating in the presence of an inert organic solvent and a tertiary organic amine to obtain a compound of the formula

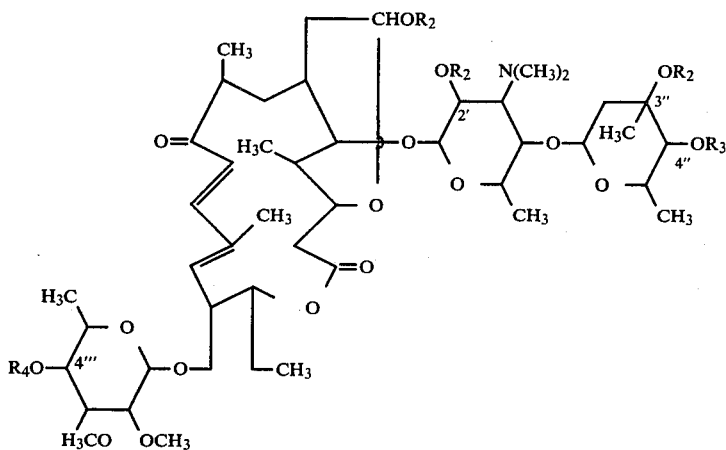

[3]

wherein $R_2$, $R_3$ and $R_4$ have the same meanings hereinbefore. Then the said compound [3] is treated with ammonia in methanol or ethanol, then treated by heating in methanol.

The introduction of protective groups to the hydroxyl groups at positions 3, 2" and 4''' can be effected by reacting with an aliphatic carboxylic acid anhydride in the presence of an inorganic base.

Examples of the above aliphatic carboxylic acid anhydrides [$(R_2)_2O$] are lower aliphatic acid anhydrides such as acetic anhydride, propionic anhydride, butyric anhydride and isovaleric anhydride.

Examples of inorganic bases are alkali hydroxides such as potassium hydroxide or sodium hydroxide, alkali carbonates such as potassium carbonate or sodium carbonate, and alkali hydrogen carbonates such as sodium hydrogen carbonate. Particularly preferred are alkali carbonates.

The introduction of the protective group is performed at 30°–100° C., preferably at 40°–60° C. The reaction progress can be checked by thin layer chromatography and the reaction can be terminated upon the disappearance of tylosin.

In the above reaction, the aldehyde group at position 18 is acylated and the hydroxyl group at position 3 is protected by ring closure between the carbon atom at position 18 and the oxygen atom at position 3; and simultaneously positions 2', 4" and 4''' are acylated.

In the above introduction of the hydroxyl group, the hydroxyl group at position 4''' alone is previously protected by halo lower alkanoyl, and thereafter the remaining hydroxyl groups at positions 3, 2" and 4" may be acylated by the above introducing of a protective group.

Preferred examples of halo lower alkanoyls are chloroacetyl, dichloroacetyl or trichloroacetyl. Introduction of the protective group is performed by reacting with 1.2–1.5 molar excess of a chlorinated aliphatic carboxylic acid halide in an inert organic solvent such as dichloromethane in the presence of a tertiary organic amine such as pyridine.

The thus-obtained 4"-halo lower alkanoyl tylosin is protected as to the hydroxyl groups at positions 3 and 2' and the hydroxyl group at position 4" is acylated by the above introduction of protective groups.

By the above introduction of protective groups, the hydroxyl groups at postions 3, 2' and 4''' are protected and the hydroxyl group at position 4" is acylated.

The product [2] can be isolated from the reaction mixture by pouring the reaction mixture into water, adjusting the water layer to pH 8-10 and extracting with a suitable water-immiscible organic solvent. Further purification can be effected by chromatography on an adsorbent such as silica gel, active alumina or adsorbent resin and eluting with a suitable solvent such as benzene-acetone.

The next step of 3"-acylation of compound [2] can be effected by reacting with an aliphatic carboxylic acid anhydride in the presence of a tertiary organic amine under heating.

Examples of the above aliphatic carboxylic acid anhydrides [(R$_3$)$_2$O] are C$_{2-6}$ aliphatic acid anhydrides such as acetic anhydride, propionic anhydride, butyric anhydride, isobutyric anhydride, valeric anhydride, isovaleric anhydride or hexanoic anhydride. Examples of tertiary organic amines are preferably pyridinic compounds such as pyridine, picoline or collidine; however these examples are not to be taken as limiting, and the other known tertiary organic amines can be used as desired. Heating temperatures may be 50°-120° C., preferably at 80°-100° C. Reaction time may depend on the heating temperature; however, reaction can be checked by silica gel thin layer chromatography and the reaction can be terminated by disappearance of the compound [2] in the reaction mixture. Usually the reaction time is in the range of 1-100 hours.

As a result of the above reaction, the previous acyl group R$_2$ at position 4" is rearranged to position 3" and the acyl group R$_3$ is introduced into position 4" by the above acylation reaction.

Isolation and purification can be conducted according to the same procedure as in processes for obtaining compound [2].

The removal of the protective groups of compound [3] is preformed by treating compound [3] with methanol or ethanol which contains ammonia to remove the protective group at positions 3 and 18 and the protective group at position 4'''. The removal reaction can proceed at room temperature. The reaction can be terminated upon the disappearance of compound [3] as determined by silica gel thin layer chromatography.

The product obtained by distilling off ammonia and alcohol from the reaction mixture is heated with methanol, which may contain water, to remove the acyl group at position 2'. Heating is under reflux in methanol. The end of the reaction can be detected by silica gel thin layer chromatography.

The compound [1a] can be obtained by isolation and purification as described above, from the product obtained by distilling off methanol in the reaction mixture.

Isolation and purification of compound [1a] are performed by any conventional procedure such as concentration, extraction, washing, transfer, crystallization, and by chromatography such as on silica gel, active alumina or an adsorption resin.

Process B: A compound wherein R$_1$ is hydrogen, i.e. a compound of the formula

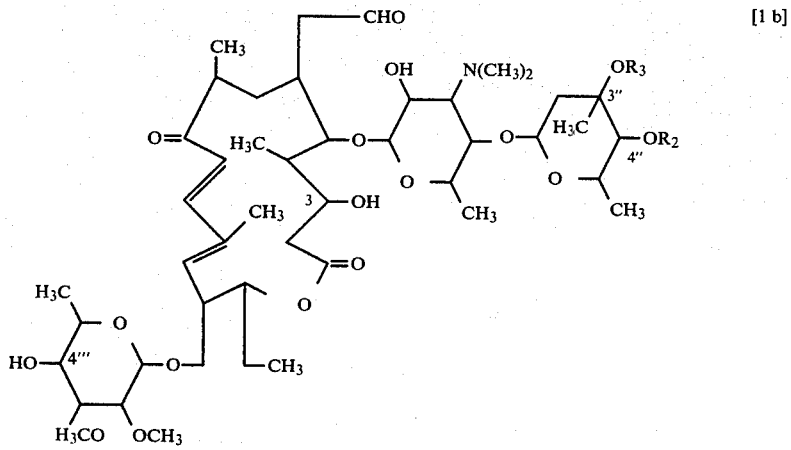

[1 b]

wherein R$_2$ and R$_3$ have the same meanings hereinbefore, can be obtained by reacting compound [2] with an aliphatic carboxylic acid halide in the presence of a tertiary organic amine in an inert organic solvent under heating to prepare a compound of the formula

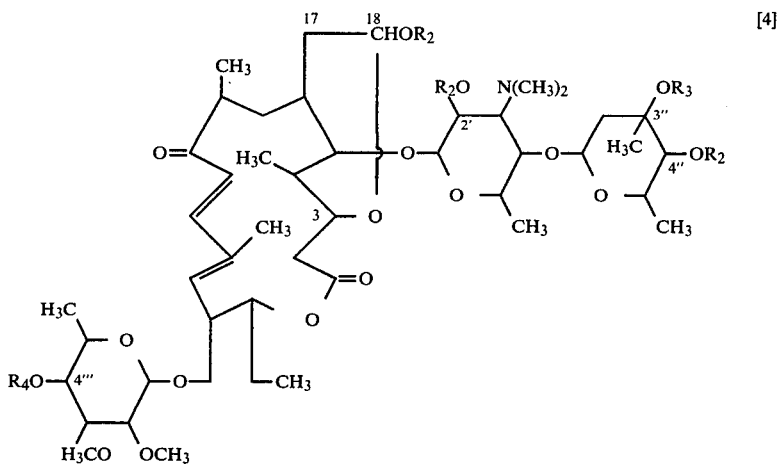

[4]

wherein $R_2$, $R_3$ and $R_4$ have the same meanings hereinbefore, and treating with a methanol or ethanol solution of ammonia, then treating in methanol under heating.

Compound [2] hereinbefore is acylated at position 3" by an aliphatic carboxylic acid halide. The acylation is performed by reacting with the corresponding aliphatic carboxylic acid halide in the presence of a tertiary organic amine in an inert organic solvent under heating. Examples of inert organic solvents are acetone, methyl ethyl ketone, ethyl acetate, dimethoxy ethane, tetrahydrofuran, dioxane, benzene or toluene. Examples of tertiary organic amines are pyridinic compounds such as pyridine, picoline or collidine; however, the other known tertiary organic amines such as triethylamine dimethylaniline, N-methylpiperidine, N-methylmorpholine, quinoline, isoquinoline or tribenzylamine can selectively be used. The corresponding carboxylic acid halide is a $C_{2-6}$ aliphatic carboxylic acid halide such as acetylchloride, propionylchloride, butyrylchloride, isobutyrylchloride, valerylchloride, isovalerylchloride or hexanoylchloride.

The heating temperature may be 50°–120° C. The reaction time can be varied depending on the reaction temperature; and since the progress of the reaction can be checked by silica gel thin layer chromatography, the end point can be determined, which will be within the range of 1 to 150 hours.

The thus-obtained compound [4] can be isolated in that, when the reaction solvent is a water-miscible organic solvent, the reaction mixture is adjusted by addition of alkali to pH 8–10 in water to form a precipitate, which is filtered out. When the reaction solvent is a water-immiscible organic solvent, the reaction mixture is poured into water, the pH adjusted to 8–10, then the water-immiscible organic solvent is separated. Further purification can be effected by chromatography using silica gel, active alumina or adsorption resin with elution such as with benzene-acetone.

The compound [1b] can be obtained by removing the protective groups at positions 3, 2' and 4'" in the reaction product [4], by the same procedure as the above process. Compound [1b] can be obtained by separation and purification after distilling off methanol.

Process C: A compound wherein $R_1$ is lower alkanoyl, i.e. a compound of the formula

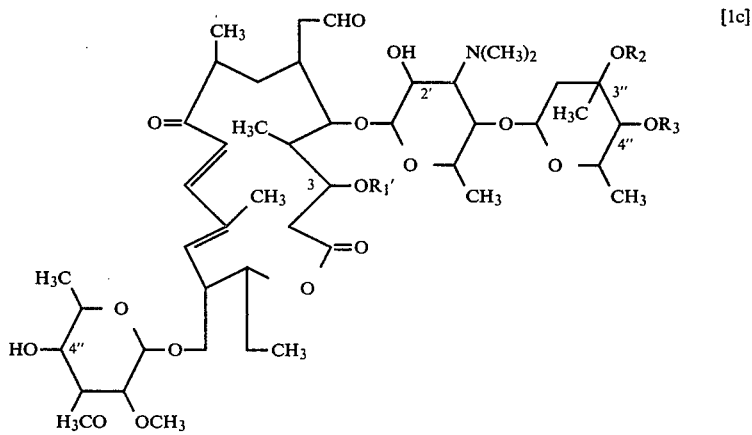

[1c]

wherein $R_1$ is lower alkanoyl and $R_2$ and $R_3$ have the same meanings hereinbefore, is prepared by acylating a 2'-acyltylosin of the formula

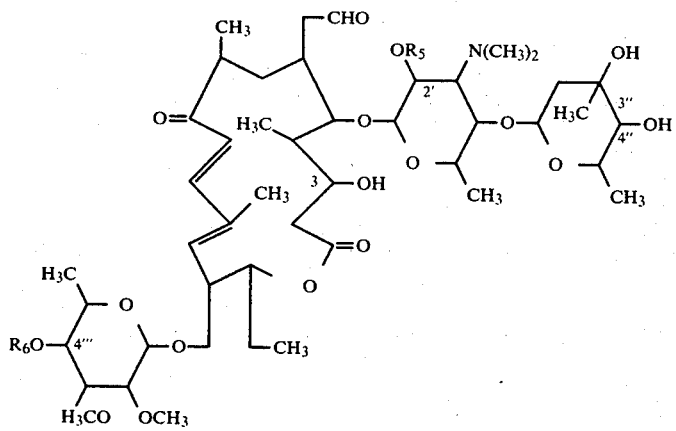

[5]

wherein $R_5$ is $C_{2-6}$ alkanoyl and $R_6$ is hydrogen, $C_{2-6}$ alkanoyl or halo lower alkanoyl, with an aliphatic carboxylic acid halide in the presence of a tertiary organic amine in an inert organic solvent to prepare a compound of the formula

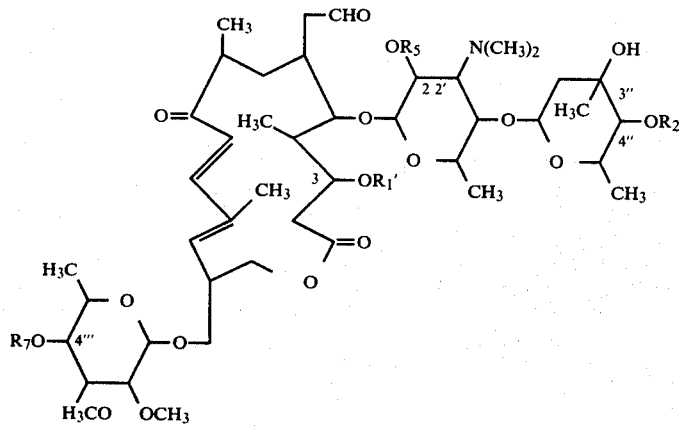

[6]

wherein $R_7$ is $C_{2-6}$ alkanoyl or halo lower alkanoyl and $R'_1$, $R_2$ and $R_5$ have the same meanings hereinbefore, and acylating the compound [6] with an aliphatic carboxylic acid anhydride in the presence of a base under heating to prepare a compound of the formula

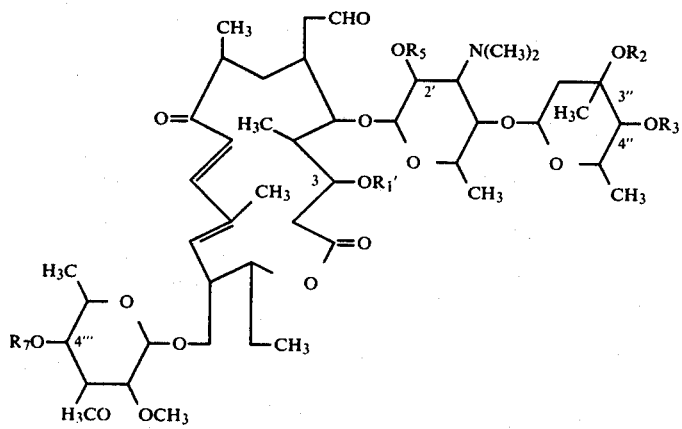

[7]

wherein $R_1$, $R_2$, $R_3$ and $R_7$ have the same meanings hereinbefore. The said compound [7] is then treated by ammonia in methanol or ethanol, and heated in methanol.

Starting material [5] is usually a known 2'-acyltylosin. The acyl group is removed in the following reaction and is $C_{2-6}$ alkanoyl, preferably acetyl, propionyl or butyryl.

The hydroxyl group at position 4''' of the above 2'-acyltylosin can optionally be protected by a $C_{2-6}$ alkanoyl group or a halo lower alkanoyl group, especially in the latter case a group such as chloroacetyl, dichloroacetyl or trichloroacetyl; however it need not always be protected.

The above 2'-acyltylosin is 3, 4"-acylated by use of the corresponding aliphatic carboxylic acid halide. The acylation is performed by reacting with the corresponding carboxylic acid halide in an inert organic solvent in the presence of a tertiary organic amine. Examples of inert organic solvents are acetone, methyl ethyl ketone, ethyl acetate, tetrahydrofuran, dioxane, benzene or toluene. Examples of tertiary organic amines are pyridinic compounds such as pyridine, picoline or collidine. Other known tertiary organic amines such as triethylamine, dimethylaniline, N-methylpiperidine, N-methylmorpholine, quinoline or isoquinoline can be used. Examples of aliphatic carboxylic halides are $C_{2-6}$ aliphatic carboxylic acid halides such as acetylchloride, propionylchloride, butyrylchloride, isobutyrylchloride, valerylchloride, isovalerylchloride or hexanoylchloride. The preferred acyl group for position-3 is a lower acyl group such as acetylchloride or propionylchloride. The reaction can proceed at room temperature and therefore it is not necessary to heat, or at most to heat 30°–5° C. The progress of the reaction can be checked by silica gel thin layer chromatography and is complete within 1–10 hours.

By the above acylation reaction, not only the hydroxyl groups at postions 3 and 4" but also that at position 4''' are acylated. Therefore the amount of aliphatic carboxylic acid halide can be determined by the number of hydroxyl groups to be acylated.

Furthermore, if the postions 3 and 4" are to be acylated by different acyl groups, a little less amount of aliphatic carboxylic acid halide is used to obtain at first the 4"-acylated compound, and thereafter the said compound is acylated with the desired aliphatic carboxylic acid halide.

The thus-obtained compound [6] can be isolated in that, when the reaction solvent is a water-miscible organic solvent, the reaction mixture is adjusted by addition of alkali to pH 8–10 in water to form a precipitate, which is filtered out. When the reaction solvent is a water-immiscible organic solvent, the reaction mixture is poured into water, the pH adjusted to 8–10; then extraction is performed with a suitable water-immiscible organic solvent. Further purification can be effected by chromatography using silica gel, active alumina or adsorption resin with elution such as with benzene-acetone.

Acylation of the product [6] at position-3" is performed by reacting with an aliphatic carboxylic acid anhydride in the presence of a base under heating. Examples of the base are alkali carbonates such as potassium carbonate or sodium carbonate, and tertiary organic amines, for example pyridinic compounds such as pyridine, picoline or collidine; however it is not so limited, and the prior known alkali carbonates, alkaline hydrogen carbonates or tertiary organic amines can be used. The aliphatic carboxylic acid anhydrides are exemplified as in process A hereinbefore. The heating reaction temperature is about 50°–120° C., preferably 80°–100° C. The reaction time varies depending on the reaction temperature; and since the reaction progress can be checked by silica gel thin layer chromatography, the end point of the reaction can be determined by disappearance of compound [6] in the reaction mixture, which occurs within 1–100 hours.

By the above reaction, the acyl group ($R_2$) initially at position-4" is rearranged to position-3", and the acyl group ($R_3$) is introduced into position-4".

Isolation and purification of compound [7] from the reaction mixture can be effected by the same procedure as described in the process for obtaining compound [4] hereinbefore.

Removal of protective group in compound [7] is performed by treating with methanol or ethanol containing ammonia to remove the protective group at position-4'''. The reaction proceeds at room temperature, and its end point is marked by the disappearance of compound [7] as detected by silica gel thin layer chromatography. Ammonia and alcohol are distilled off from the thus-obtained reaction mixture and the mixture is heated in methanol which may contain water to remove the acyl group at position-2'. Heating is conducted under reflux of methanol. The reaction progress can be chedk by silica gel thin layer chromatography to detect the end point of the reaction.

The compound [1d] can be obtained by isolation and purification of the reaction mixture after methanol is distilled off.

Process D: A compound wherein $R_1$ is lower alkanoyl, i.e. a compound of the formula

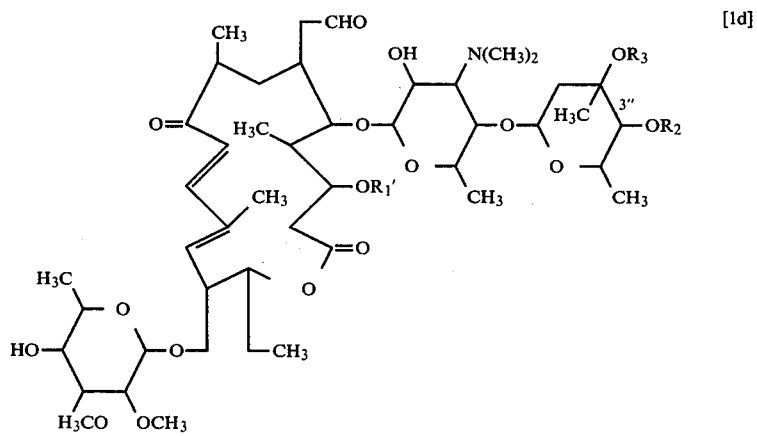

[1d]

wherein $R'_1$, $R_2$ and $R_3$ have the same meanings hereinbefore, can be prepared as follows:

The compound [6] is acylated by heating with an aliphatic carboxylic halide in the presence of a tertiary organic amine in an inert organic solvent to prepare the compound [8] of the formula

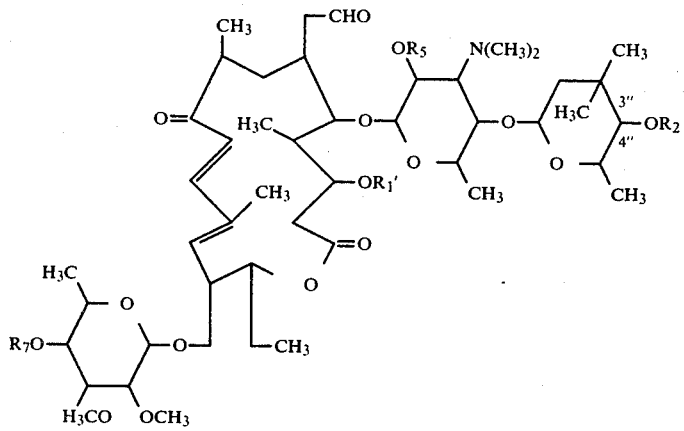

[8]

wherein $R'_1$, $R_2$, $R_3$, $R_5$ and $R_7$ have the same meanings hereinbefore. The said compound [8] is treated with ammonia in methanol or ethanol, then heated in methanol.

To obtain compound [8], compound [6] is acylated at position-3″ with an aliphatic carboxylic acid halide.

Also the said acylation can be performed by the same process as the 3″-acylation of compound [2] as in process A hereinbefore.

Next, the protective groups at position 2′ and 4″ in compound [8] are removed to obtain compound [1d]. The said removal can be performed by the same removal reaction as for the protective group in compound [7] hereinbefore. Compound [1d] can be obtained by isolation and purification as described blow, from the product after removing methanol.

Isolation of the desired compound [1] can be performed by known methods for the isolation and purification of macrolide antibiotics, for example: concentration, extraction, washing, transfer and recrystallization, and chromatography using silica gel, active alumina or an adsorbent such as an adsorbent resin.

In Table I hereinafter is shown the minimum inhibitory concentrations (MIC) on microorganisms of the products of the present invention. As a result, the compound [1] is seen to be effective against macrolide-resistant A group microorganisms.

The following examples illustrate the production of compound [1] of the present invention:

Rf values in the examples are measured, if not specified, by the following thin layer chromatography:

Carrier: silica gae 60 (Art 5721, Merck Co.)
Developer:
A: n-hexane-acetone-benzene-ethyl acetate-methanol (30:10:25:20:10)
B: benzene-acetone (3:1)
c: benzene-acetone (4:1)

TABLE 1

| MIC μg/ml | | Compound of the present invention | | | | | | | | | Control | |
|---|---|---|---|---|---|---|---|---|---|---|---|---|
| compound test organisms | 3″-position 4″-position | Ac Ac | Ac Pro | Ac Bu | Ac Iva | Ac Hex | Pro Pro | Pro Bu | Pro Iva | Bu Bu | Iva Ac | H H | H Bu |
| Staph.aureus ATCC6538P | | 0.8 | 1.6 | 1.6 | 1.6 | 1.6 | 1.6 | 1.6 | 1.6 | 1.6 | 0.8 | 0.8 | 0.8 |
| Staph.aureus MS353 | | 1.6 | 3.1 | 3.1 | 3.1 | 3.1 | 3.1 | 3.1 | 3.1 | 6.1 | 1.6 | 1.6 | 3.1 |
| Staph.aureus MS353A0* | | 12.5 | 25 | 12.5 | 6.3 | 12.5 | 25 | 12.5 | 6.3 | 12.5 | 6.3 | >100 | 50 |
| Staph.aureus 0116* | | 12.5 | 6.3 | 6.3 | 6.3 | 6.3 | 6.3 | 6.3 | 6.3 | 6.3 | 6.3 | >100 | 25 |
| Staph.aureus 0119* | | 50 | 12.5 | 12.5 | 6.3 | 12.5 | 12.5 | 12.5 | 6.3 | 12.5 | 25 | >100 | 50 |
| Staph.aureus 0127* | | 100 | 25 | 25 | 12.5 | 25 | 25 | 25 | 12.5 | 25 | >100 | >100 | 100 |
| Strept.pyogenes N.Y.5 | | 0.2 | 0.2 | 0.2 | 0.2 | 0.4 | 0.2 | 0.2 | 0.4 | 0.2 | 0.2 | 0.2 | 0.2 |
| Strept.pyogenes 1022* | | 6.3 | 1.6 | 1.6 | 1.6 | 1.6 | 1.6 | 1.6 | 0.8 | 1.6 | 6.3 | >100 | 12.5 |

*Erythromycin, oleandomycin, 16-membered macrolide resistant strains of clinical isolates (macrolide-resistant A-group strains)
Ac: acetyl,
Pro: propionyl,
Bu: butyryl,
Iva: isovaleryl,
Hex: hexanoyl.

EXAMPLE 1

3″-acetyl-4″-butyryltylosin:

Potassium carbonate (7 g) was added to tylosin (10 g) dissolved in acetic anhydride (20 ml) and stirred for 24 hours at 60° C. The reaction mixture was poured into water (200 ml), adjusted to pH 9.5 by adding aqueous ammonia, and extracted twice with chloroform (100 ml). The extract was dried with anhydrous magnesium sulfate and further dried in vacuo to obtain crude 18, 2′, 4″, 4‴-tetraacetyl-3, 18-O-cyclo-tylosin (10.2 g).

TLC: $Rf_A=0.75$, $Rf_B=0.49$, $Rf_C=0.34$.
(TLC of tylosin: $Rf_A=0.20$, $Rf_B=0.01$, $Rf_C=0.01$)
Mass: 1083 (M+), 1024 (M+−59)

Butyric anhydride (4 ml) was added to the above product (10 g) dissolved in dry pyridine (50 ml) and stirred for 4 days at 100° C. The reaction mixture was poured into water (400 ml) and extracted twice with chloroform (200 ml). The extract was dried with anhydrous magnesium sulfate, and further dried in vacuo to obtain crude 18, 2′, 3″, 4‴-tetraacetyl-3, 18-O-cyclo-4″-butyryltylosin (9.8 g).

TLC: $Rf_B=0.77$, $Rf_C=0.61$.

The said product was chromatographed on silica gel with elution with benzene-acetone (15:1) to obtain an eluate showing the above Rf value to yield the purified product (3.5 g). This was dissolved in methanol (30 ml) and methanol saturated with ammonia (20 ml) was added thereto and the mixture was then stirred for 8 hours at room temperature.

Water was added to the reaction mixture, which was extracted twice with chloroform (150 ml). The extract was dried with anhydrous magnesium sulfate and further dried in vacuo. The residue was dissolved in methanol (150 ml), refluxed for 12 hours and dried in vacuo. The residue was chromatographed on a silica gel column and eluted with benzene-acetone (9:1) and benzene-acetone (7:1). The eluate obtained by the former method was dried in vacuo to obtain 3″, 4″-diacetyl-4″-butyryltylosin (TLC: $Rf_A=0.71$, 400 mg), and the eluate obtained by the latter method was dried in vacuo to obtain 3″-acetyl-4″-butyryltylosin (2.5 g).

TLC: $Rf_A=0.57$.

Mass: 922 (M+ −87−18).

NMR (100 MHz in CDCl$_3$): 1.39 (3″CH$_3$), 1.76 (12 CH$_3$) 1.96 (3″OAc), 2.51 [3′N(CH$_3$)$_2$], 3.44 (2‴OCH$_3$), 3.56 (3‴OCH$_3$), 9.57 (18 CHO) ppm.

EXAMPLE 2

3″-acetyl-4″-propionyltylosin:

In Example 1, butyric anhydride was replaced by propionic anhydride to obtain 3″-acetyl-4″-propionyltylosin via 18, 2′, 3″, 4‴-tetraacetyl-3, 18-O-cyclo-4″-propionyltylosin (TLC: $Rf_B=0.75$, $Rf_C=0.59$).

TLC: $Rf_A=0.55$.

Mass: 1013 (M+).

NMR (100 MHz in CDCl$_3$): 1.39 (3″CH$_3$), 1.76 (12 CH$_3$), 1.96 (3″OAc), 2.51 [3′N(CH$_3$)$_2$], 3.44 (2‴OCH$_3$), 3.56 (3‴OCH$_3$), 9.56 (18 CHO) ppm.

EXAMPLE 3

3″, 4″-diacetyltylosin:

In Example 1, butyric anhydride was replaced by acetic anhydride to obtain 3″, 4″-diacetyltylosin via 18, 2″, 3″, 4″, 4‴-pentaacetyl-3, 18-O-cyclo-tylosin (TLC: $Rf_B=0.71$, $Rf_C=0.55$).

TLC: $Rf_A=0.53$.

Mass: 981 (M+ −18).

NMR (100 MHz in CDCl$_3$): 1.39 (3″CH$_3$), 1.75 (13CH$_3$), 1.97 (3″OAc), 2.11 (4″OAc), 2.51 [3′N(CH$_3$)$_2$], 3.44 (2‴OCH$_3$), 3.56 (3‴OCH$_3$), 9.56 (18CHO) ppm.

EXAMPLE 4

3″-acetyl-4″-hexanoyltylosin:

In Example 1, butyric anhydride was replaced by hexanoic anhydride to obtain 3″-acetyl-4″-hexanoyltylosin via 18, 2′, 3″, 4‴-tetraacetyl-3, 18-O-cyclo-4″-hexanoyltylosin (TLC: $Rf_B=0.80$, $Rf_C=0.65$).

TLC: $Rf_A=0.61$.

Mass: 922 (M+ −115−18), 390

NMR (100 MHz in CDCl$_3$): 1.39 (3″CH$_3$), 1.76 (12CH$_3$), 1.96 (3″OAc), 2.52 [3′N(CH$_3$)$_2$], 3.43 (2‴OCH$_3$), 3.55 (3‴OCH$_3$), 9.55 (18CHO) ppm.

EXAMPLE 5

4″-isovaleryl-3″-propionyltylosin:

Anhydrous potassium carbonate (37.7 g) was added to tylosin (50 g) dissolved in propionic anhydride (139.8 ml) and stirred for 24 hours at 60° C. The reaction mixture was poured into water (500 ml), adjusted to pH 9.5 by adding aqueous ammonia and extracted twice with chloroform (300 ml). The extract was washed with water, dried by adding anhydrous magnesium sulfate and further dried in vacuo to obtain crude 3, 18-O-cyclo-18, 2′, 4″, 4‴-tetrapropionyltylosin (48.5 g).

TLC: $Rf_A=0.84$, $Rf_B=0.74$, $Rf_C=0.57$.

Isovaleric anhydride (4.5 ml) was added to the above product (10 g) dissolved in dry pyridine (50 ml) and stirred for 5 days at 100° C. Pyridine was distilled off in vacuo from the reaction mixture, and the residue was poured into water (200 ml), which was extracted twice with chloroform. The extract was washed with water, then aqueous ammonia (pH 9.0), dried by adding anhydrous magnesium sulfate, and further dried in vacuo to obtain crude 3, 18-O-cyclo-4″isovaleryl-18, 2′, 3″, 4‴-tetrapropionyltylosin (10.2 g).

TLC: $Rf_B=0.87$, $Rf_C=0.78$.

Methanol saturated with ammonia (50 ml) was added to this product dissolved in methanol (50 ml) and stirred for 15 hours at room temperature. The reaction mixture was poured into water (500 ml) and extracted twice with chloroform (300 ml). The extract was dried in vacuo. The residue was dissolved in methanol (100 ml) and refluxed for 17 hours. The reaction mixture was dried in vacuo to obtain the product (9.5 g), which was chromatographed on a silica gel column eluted with benzene-acetone (15:1−7:1) to obtain 4″-isovaleryl-3″,4‴-dipropionyltylosin (TLC: $Rf_A=0.79$, 100 mg) and 4″-isovaleryl-3″-propionyltylosin (2.7 g).

LC: $Rf_A$ 0.60

Mass: 981 (M+ −73), 954 (M+ −101).

NMR (100 MHz in CDCl$_3$): 1.39 (3″CH$_3$), 1.75 (12CH$_3$), 2.51 [3′N(CH$_3$)$_2$], 3.43 (2‴OCH$_3$), 3.55 (3‴OCH$_3$), 9.56 (18 CHO) ppm.

EXAMPLE 6

4″-butyryl-3″-propionyltylosin:

In Example 5, isovaleric anhydride was replaced by butyric anhydride to obtain 4″-butyryl-3″-propionyltylosin via 4″-butyryl-3, 18-O-cyclo-18, 2′, 3″, 4‴-tetrapropionyltylosin [TLC: $Rf_B=0.87$, $Rf_C=0.78$, NMR (100 MHz in CDCl$_3$): 1.39 (3″CH$_3$), 1.72 (12CH$_3$), 2.36 (3′N(CH$_3$)$_2$), 3.39 (2‴OCH$_2$), 3.46 (3‴OCH$_3$) ppm].

TLC: $Rf_A=0.58$.

Mass: 954 (M+ −87).

NMR (100 MHz in CDCl$_3$): 1.39 (3″CH$_3$), 1.76 (12CH$_3$), 2.51 [3′N(CH$_3$)$_2$], 3.44 (2‴OCH$_3$), 3.56 (3‴OCH$_3$), 9.56 (18CHO) ppm.

EXAMPLE 7

3″, 4″-dipropionyltylosin:

In Example 5, isovaleric anhydride was replaced by propionic anhydride to obtain 3″, 4″-dipropionyltylosin via 3, 18-O-cyclo-18, 2′, 3″, 4″, 4‴-pentapropionyltylosin [TLC: $Rf_B=0.86$, $Rf_C=0.76$, NMR (100 MHz in CDCl$_3$): 1.39 (3″CH$_3$), 1.69 (13CH$_3$), 2.36 (3′N(CH$_3$)$_2$), 3.39 (2‴OCH$_3$), 3.46 (3‴OCH$_3$) ppm].

TLC: $Rf_A=0.58$.

Mass: 954 (M+ −73).

NMR (100 MHz in CDCl$_3$): 1.39 (3″CH$_3$), 1.75 (12CH$_3$), 2.51 [3′N(CH$_3$)$_2$], 3.44 (2‴OCH$_3$), 3.56 (3‴OCH$_3$), 9.55 (18CHO) ppm.

EXAMPLE 8

3″, 4″-dibutyryltylosin:

Anhydrous potassium carbonate (7.5 g) was added to tylosin (10 g) dissolved in butyric anhydride (28 ml) and stirred for 24 hours at 60° C. The reaction mixture was poured into water (100 ml) and extracted twice with chloroform (100 ml). The extract was washed with water, dried by adding anhydrous magnesium sulfate and further dried in vacuo to obtain 18, 2', 4", 4'"-tetrabutyryl-3, 18-O-cyclo-tylosin crude powder (9.8 g). TLC: $Rf_B=0.86$, $Rf_C=0.74$.

Butyric anhydride (4 ml) was added to this crude powder dissolved in dry pyridine (50 ml) and stirred for 102 hours at 100° C. The reaction mixture was poured into water (400 ml) and extracted twice with chloroform (200 ml). The extract was dried by adding anhydrous sodium sulfate and further dried in vacuo to obtain crude 18, 2', 3", 4", 4'"-pentabutyryl-3, 18-O-cyclotylosin (8.9 g).

TLC: $Rf_B=0.89$, $Rf_C=0.83$.

The crude powder was chromatographed on a silica gel column by eluting with benzene-acetone (19:1) at the above Rf value to obtain the purified product (2.9 g) after drying in vacuo.

Methanol saturated with ammonia (25 ml) was added to the product dissolved in methanol (25 ml) and stirred for 10 hours at room temperature. Water was added to the reaction mixture, which was then extracted twice with chloroform (150 ml). The extract was dried by adding anhydrous sodium sulfate and further dried in vacuo. The residue, dissolved in methanol (150 ml), was refluxed for 17 hours and dried in vacuo. The residue was chromatographed by silica gel column chromatography by eluting with benzene-acetone (15:1–7:1) to obtain 3", 4"-dibutyryltylosin (2.3 g).

TLC: $Rf_A=0.60$.

Mass: 1055 (M+).

NMR (100 MHz in CDCl$_3$): 1.39 (3"CH$_3$), 1.76 (12CH$_3$), 2.51 [3'N(CH$_3$)$_2$], 3.44 (2'"OCH$_3$), 3.56 (3'"OCH$_3$), 9.56 (18CHO) ppm.

EXAMPLE 9

4"-acetyl-3"-isovaleryltylosin:

γ-collidine (13.42 ml) and isovalerylchloride (11.29 ml) were added to 18, 2', 4", 4'"-tetraacetyl-3, 18-O-cyclo-tylosin (10 g) described in Example 1 dissolved in dry dioxane and stirred at 90° C. for 45 hours. The reaction mixture was poured into ice water (300 ml) and extracted twice with chloroform (200 ml). The extract was washed with 0.1 N HCl, and then diluted aqueous ammonia and water, dried by adding anhydrous sodium sulfate and further dried in vacuo to obtain crude 18, 2', 4", 4'"-tetraacetyl-3,8-O-cyclo-3"-isovaleryltylosin (10.2 g).

TLC: $Rf_B=0.76$, $Rf_C=0.61$

The crude product was chromatographed on a silica gel column by eluting with benzene-acetone (15:1) and the eluate showing the above RF value was dried in vacuo to obtain the purified product (4.1 g).

Methanol saturated with ammonia (100 ml) was added to the said product dissolved in methanol (100 ml) and stirred for 12 hours at room temperature. The reaction mixture was poured into ice water (500 ml) and extracted twice with chloroform (300 ml). The extract was dried by adding anhydrous magnesium sulfate and further dried in vacuo. The residue was dissolved in methanol (100 ml), refluxed for 18 hours and dried in vacuo. The thus-obtained residue was eluted with benzene-acetone (7:1) and the corresponding active fractions were collected and dried in vacuo to obtain 4", 4'"-diacetyl-3"-isovaleryltylosin (TLC: $Rf_A=0.73$, 0.2 g) and 4"-acetyl-3"-isovaleryltylosin (3.2 g).

TLC: $Rf_A=0.57$.

Mass: 1041 (M+).

NMR (100 MHz in CDCl$_3$): 1.39 (3" CH$_3$), 1.77 (13CH$_3$), 2.11 (4"OAc), 2.51 [3'N(CH$_3$)$_2$], 3.44 (2'"OCH$_3$), 3.56 (3'"OCH$_3$), 9.56 (18CHO) ppm.

EXAMPLE 10

3, 3"-diacetyl-4"-butyryltylosin:

Acetic anhydride (8.5 ml) was added to tylosin (10 g) dissolved in dry acetone (50 ml) and stirred for 4 hours at room temperature. The reaction mixture was poured into water (200 ml), adjusted to pH 9.5 by adding aqueous ammonia and extracted twice with chloroform (200 ml). The extract was dried by adding anhydrous magnesium sulfate and further dried in vacuo to obtain 2'-acetyltylosin (10.2 g). TLC: $Rf_b=0.12$, $Rf_C=0.06$. (Tylosin: $Rf_A$ 0.20, $Rf_B$ 0.01, $Rf_C$ 0.01).

Dry pyridine (8.05 ml) and acetylchloride (6.4 ml) were added to the above product (10 g) dissolved in dry acetone (50 ml) and stirred for 150 minutes at 45° C. The reaction mixture was poured into water (200 ml), adjusted to pH 9.5 by adding aqueous ammonia, and the precipitate was filtered to obtain 3, 2', 4", 4'"-tetraacetyltylosin (8.44 g). TLC: $Rf_B=0.40$, $Rf_C=0.22$.

Butyric anhydride (1 ml) was added to the above product (2.0 g) dissolved in dry pyridine (10 ml) and stirred for 4 days at 100° C. The reaction mixture was poured into water (50 ml), adjusted to pH 9.5 by adding aqueous ammonia and extracted with chloroform (50 ml). The extract was washed twice with 0.1 N HCl (50 ml) and once with diluted aqueous ammonia, washed with anhydrous magnesium sulfate and dried in vacuo to obtain crude 3, 2', 3", 4'"-tetraacetyl-4"-butyryltylosin. TLC: $Rf_B=0.81$, $Rf_C=0.66$.

Methanol saturated with ammonia (10 ml) was added to this crude product dissolved in methanol and stirred for 3 hours under ice cooling. The reaction mixture was poured into water (100 ml) and extracted with chloroform (100 ml). The extract was dried by adding anhydrous magnesium sulfate and dried in vacuo. The residue was dissolved in methanol (50 ml), refluxed for 17 hours and dried in vacuo to obtain crude 3, 3"-diacetyl-4"-butyryltylosin. This was purified by silica gel column chromatography by eluting with benzene-acetone (10:1) to yield the purified product (1.2 g). TLC: $Rf_A=0.73$.

EXAMPLE 11

3, 3"-diacetyl-4"-isovaleryltylosin:

In Example 10, butyric anhydride was replaced by isovaleric anhydride to obtain 3, 3"-diacetyl-4"-isovaleryltylosin. TLC: $Rf_A=0.76$.

EXAMPLE 12

3"-acetyl-4"-isovaleryltylosin:

Potassium carbonate (7 g) was added to tylosin (10 g) dissolved in acetic anhydride (20 ml) and stirred for 24 hours at 60° C. The reaction mixture was poured into water (200 ml), adjusted to pH 9.5 by adding aqueous ammonia and extracted twice with chloroform (100 ml). The extract was dried with anhydrous magnesium sulfate and further dried in vacuo to obtain crude 18, 2', 4", 4'"-tetraacetyl-3, 18-O-cyclo-tylosin [$Rf_B=0.49$, Mass: 1084 (M+)](10.2 g).

Isovaleric anhydride (4 ml) was added to the crude product dissolved in dry pyridine (50 ml) and stirred for 110 hours at 100° C. The reaction mixture was poured into water (400 ml) and extracted twice with chloroform (200 ml). The extract was dried with anhydrous magnesium sulfate and further dried in vacuo to obtain crude 18, 2', 3'', 4'''-tetraacetyl-3, 18-O-cyclo-4''-isovaleryltylosin [$Rf_B=0.76$, Mass: 1168 (M+)]. The said product was chromatographed on a silica gel column by eluting with benzene-acetone (15:1). Fractions showing $Rf_B=0.76$ were collected and dried to obtain the purified product (2.8 g).

Methanol saturated with ammonia (20 ml) was added to this product dissolved in methanol (20 ml) and stirred for 5 hours at room temperature. Water (200 ml) was added to the reaction mixture, which was then extracted twice with chloroform (100 ml). The extract was dried with anhydrous magnesium sulfate and further dried in vacuo. The residue was dissolved in methanol (100 ml) and refluxed for 12 hours. The reaction mixture was dried in vacuo and the residue was chromatographed on a silica gel column by eluting with benzene-acetone (9:1) and benzene-acetone (7:1), respectively. The former eluate was dried in vacuo to obtain 3'', 4''-diacetyl-4''-isovaleryltylosin [$Rf_B=0.39$, Mass: 1084 (M+)](320 mg). The latter eluate was dried in vacuo to obtain the desired 3''-acetyl-4''-isovaleryltylosin (1.2 g).

$Rf_B=0.23$.

Mass: 1042 (M+).

What we claim:

1. A compound of the formula

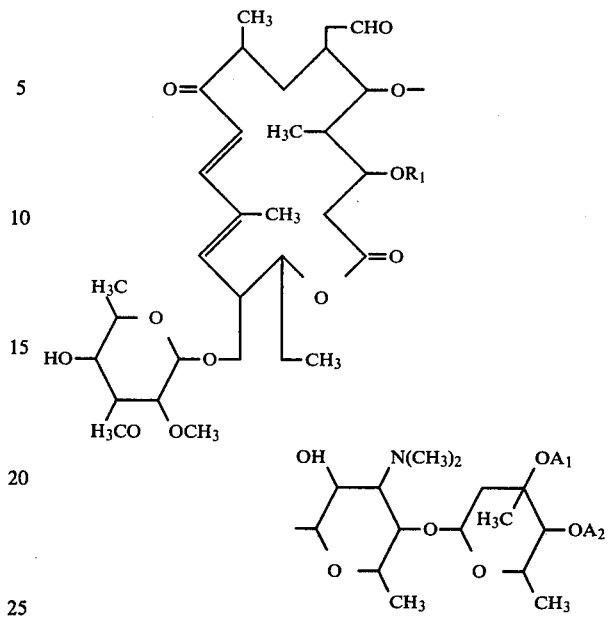

wherein $R_1$ is hydrogen or lower alkanoyl, $A_1$ and $A_2$ are groups of which one is $R_2$ and the other is $R_3$, and $R_2$ and $R_3$ are $C_{2-6}$ alkanoyl, or a physiologically acceptable salt thereof.

2. A compound claimed in claim 1 wherein $R_1$ is hydrogen, or a physiologically acceptable salt thereof.

3. A compound claimed in claim 2 wherein $A_1$ is acetyl, propionyl, butyryl, or isovaleryl and $A_2$ is acetyl, propionyl, butyryl, isobutyryl, valeryl, isovaleryl or hexanoyl, or a physiologically acceptable salt thereof.

4. A compound claimed in claim 3, which is 3'', 4''-diacetyltylosin, 3''-acetyl-4''-propionyltylosin, 3''-acetyl-4''-butyryltylosin, 3''-acetyl-4''-isovaleryltylosin, 3''-acetyl-4''-hexanoyltylosin, 3'', 4''-dipropionyltylosin, 4''-butyryl-3''-propionyltylosin, 4''-isovaleryl-3''-propionyltylosin, 3'', 4''-dibutyryltylosin or 4''-acetyl-3''-isovaleryltylosin, or a physiologically acceptable salt thereof.

5. A compound claimed in claim 1 wherein $R_1$ is lower alkanoyl.

6. A compound claimed in claim 5 wherein $R_1$ is acetyl or propionyl.

7. A compound claimed in claim 6 wherein $A_1$ is acetyl, propionyl, butyryl or isovaleryl, and $A_2$ is acetyl, propionyl, butyryl, isobutyryl, valeryl, isovaleryl or hexanoyl.

8. A compound claimed in claim 7, which is 3, 3'''-diacetyl-4''-butyryltylosin or 3, 3'''-diacetyl-4''-isovaleryltylosin.

* * * * *